(12) United States Patent
Ghosal

(10) Patent No.: US 7,250,181 B2
(45) Date of Patent: Jul. 31, 2007

(54) POLYHERBAL COMPOSITIONS AND METHODS FOR TREATING VIRAL INFECTIONS

(75) Inventor: Shibnath Ghosal, Calcutta (IN)

(73) Assignee: Natreon, Inc., New Brunswick, NJ (US)

( * ) Notice: Subject to any disclaimer, the term of this patent is extended or adjusted under 35 U.S.C. 154(b) by 0 days.

(21) Appl. No.: 11/038,557

(22) Filed: Jan. 19, 2005

(65) Prior Publication Data

US 2006/0159784 A1 Jul. 20, 2006

(51) Int. Cl.
*A61K 36/00* (2006.01)
(52) U.S. Cl. ...................... 424/725; 424/769
(58) Field of Classification Search ............... None
See application file for complete search history.

(56) References Cited

U.S. PATENT DOCUMENTS 6,153,198 A * 11/2000 Ghosal ................ 424/773
2003/0039662 A1* 2/2003 Ghosal ................ 424/195.15

FOREIGN PATENT DOCUMENTS

CA 2 358 013 A1 * 7/2000
GB 2314270 5/1997

OTHER PUBLICATIONS en.wikipedia.org/w/index.php?title=Antiviral_drug&printable=yes; accessed Jul. 11, 2006.*

* cited by examiner

*Primary Examiner*—Susan Hoffman
(74) *Attorney, Agent, or Firm*—Mathews, Shepherd, McKay & Bruneau, P.A.

(57) ABSTRACT

The present invention relates to pharmaceutical or veterinary or nutritional compositions of polyherbal extracts useful as anti-viral or immune-supporting agents. Particularly, the present invention of polyherbal composition comprises of extracts of *Withania somnifera, Mangifera indica* and purified Shilajit. This cost effective immune-supporting agent is ideal for use during the maintenance phase of the treatment, following an initial viral load reduction phase in which it is used as an adjuvant to conventional anti-viral drug therapy. The anti-viral and immune-supporting composition of this invention can perhaps be the sole basis of treatment where affordability is an issue. Additionally, this composition is used for the treatment, prevention or management of immune-supporting system in primates in need, especially humans.

21 Claims, No Drawings

POLYHERBAL COMPOSITIONS AND METHODS FOR TREATING VIRAL INFECTIONS

FIELD OF THE INVENTION

The present invention relates to compositions of polyherbal extracts for use as an anti-viral and/or immune-supporting agent. Particularly, the present invention of polyherbal composition comprises of extracts of two plants, comprising of *Withania somnifera* and *Mangifera indica* and purified Shilajit obtained from rock exudates.

BACKGROUND OF THE INVENTION

In the United States, more than 12 million new cases of sexually transmitted diseases (STDs) occur each year. Of the top 10 reportable diseases in the United States, five are STDs including chlamydia, gonorrhea, syphilis, the Acquired Immune Deficiency Syndrome (AIDS) and hepatitis B virus (HBV) infection of which AIDS and HBV infection have no cures.

In the case of AIDS, the World Health Organization estimates that 40 (between 34 and 46) million people worldwide are living with human immunodeficiency virus (HIV), the virus that causes (AIDS). Among the 40 million, 2.5 (between 2.1 and 2.9) million are children under the age of 15. Globally, an estimated 5 (4.2-5.8) million people were newly infected and 3 (2.5-3.5) million people died of AIDS in 2003. The incidence of HIV and AIDS is on the rise in Asia, and the CIA (Central Intelligence Agency) estimates that India will have the largest population of infected people by 2010 (Weniger B C, Brown T., The march of AIDS through Asia. N Eng J Med 1996; 335: 343-5.). Hepatitis infections affect 5 times more people than HIV. It has been reported by the World Health Organization that 2 billion people alive today are infected with HBV virus, of whom 350 million are chronically infected and therefore at risk of death from liver disease.

Although mortality rates from AIDS are dropping due to new therapies, AIDS remains the second leading cause of death in adults between the ages of 29 and 40. Combination anti-HIV therapy is now the standard of care for people with HIV. There are now 11 anti-HIV drugs available by prescription. These anti-HIV drugs fall into three categories: nucleosides analogs, which include zidovudine, didanosine, zalcitabine, stavudine and lamivudine; protease inhibitors which include indinavir, nelfinavir, saquinavir and ritonavir and non-nucleoside reverse transcriptase inhibitors (NNRTI) which include nevirapine, delavirdine and efavirenz. Compared to HIV, there is presently only two-licensed therapy for chronic hepatitis B virus infection, which are interferon and lamivudine. Other drugs are currently under clinical trials including lamivudine, famciclovir, lobucavir and adefovir. But many studies have shown that most patients relapse after completion of therapy and develop resistance to the drugs.

Development of resistance has recently become a major concern in the treatment of HIV and HBV infections. Resistance usually occurs when the drugs being used are not potent enough to completely stop virus replication. If the virus can reproduce at all in the presence of drugs, it has the opportunity to make changes in its structure, called mutations, until it finds one that allows it to reproduce in spite of the presence of the drugs. Once a mutation occurs, it then grows unchecked and soon is the dominant strain of the virus in the individual. The drug becomes progressively weaker against the new strain. There is also increasing concern about cross-resistance. Cross-resistance occurs when mutations-causing resistance to one drug also cause resistance to another. Several studies have proven that combining two drugs delays the development of resistance to one or both drugs compared to when either drug is used alone. Other studies suggest that three-drug combinations extend this benefit even further. As a result, it is commonly believed that the best way of preventing, or at least delaying resistance is to use multi-drug combination therapies. The risk of drug interactions and toxicity to the patient increases as the number of drugs increases.

The current standard care is a three-drug combination, of two nucleoside analogues and one protease inhibitor. Unfortunately, non-availability, high cost, toxicity concerns and emergence of drug resistance of present anti-viral drugs, pose difficulty in therapeutic management of many patients (K Vermani, S Garg, *J Ethnopharmacol,* 80 (1): 49-66, 2002; J. A. Wu, A S Attele, L Zhang, C S Yuan, *Am J Chin Med,* 29 (1): 69-81, 2001).

Plant extracts have also been reported to have anti-viral activity. For example, the plant extract of Buxus sempervirens (code named SPV 30) had shown beneficial effect in asymptomatic HIV patients and was found to delay the progression of HIV disease (Durant J et al., *Phytomedicine,* 5, 1-10, 1998). However, in this investigation, a very high dose (330 mg×3/day) was given to the HIV patients. A polyherbal formulation consisting of extracts of *Ocimum sanctum, Withania somnifera, Emblica officinalis* and *Tinospora cordifolia* has been reported to protect nonspecific host defence mechanisms (S Chatterjee and S N Das, *Ani Sci Life,* 16, 200-205, 1997; *Ani Sci Life,* 15 (4): 250-253, 1996). Chatterjee et al also have shown that in immunodeficient and immunocompromised host, this polyherbal preparation restored and improved the immune status. A polyherbal formulation consisting of 100 mg each of extracts of *Tinospora cordifolia, Withania somnifera, Emblica officinalis* and *Ocimum sanctum* has been reported to have a favorable effect in patients with HIV infection by decreasing the mean viral load and increasing the CD4 cell count (P R Usha, Naidu M U R, and Raju Y S N, Evaluation of Antiretroviral Activity of a New Polyherbal Drug "Immu-25" in Patients With HIV Infection, Drugs R&D, 2003, 4(2), 103-109.) U.S. Pat. No. 5,529,778 has described a composition consisting of eight different plant extracts which have beneficial effects against AIDS, flu, tuberculsis, hepatitis, cirrhosis and immunodeficiency conditions. This patent also describes the use of a very high dose (1 g×2/day) to the patients. Plant extracts are not standardized against their bioactive principles. Hence, consistency of results is expected to be compromised and questionable.

It is necessary to approach the treatment of HIV disease from as many directions as possible. Complementary therapies—nutritional intervention in particular because it enhances the immune system and reduces drug side effects—are an important aspect of HIV management. Simply taking a multivitamin, in addition to eating a nutrient-rich diet, may make the difference in an HIV-positive person's life span. For many patients, combining dietary supplements with drug cocktails may be one of the most cost-effective and beneficial therapeutic protocols. In a recent study, Lu et al have concluded that AIDS is a reversible disease and using medicinal herbs to enhance the immune function will facilitate the appearance of seroconversion, which has not been reported before (Lu W B, Wen R X, Guan C F. A report on 8 seronegative converted HIV/AIDS patients with traditional Chinese medicine. Zhongguo Zhong Xi Yi Jie He Za Zhi May 1997;17(5):271-3). Accordingly, the present invention offers one such alternative in the form of a poly-herbal formulation as a stand-alone therapy or as an adjuvant to the drug cocktails.

SUMMARY OF THE INVENTION

The present invention provides novel pharmaceutical, veterinary or nutritional compositions useful for the treatment of viral infections, or use as an adjuvant or complementary treatment to an existing or conventional anti-viral therapy. The composition comprises two plant extracts— *Withania somnifera* and *Mangifera indica* and an extract of rock exudates—purified Shilajit. In another aspect, the present invention provides these compositions in the form of standardized plant extracts—*Withania somnifera* and *Mangifera indica* and a standardized extract of rock exudates—purified Shilajit.

In another aspect, there is provided a method of treating viral infections in a subject in need of such treatment comprising administering to the subject a therapeutically effective amount of a compound or composition of the present invention, either alone or as an adjuvant, or complementary treatment to an existing anti-viral therapy.

In another aspect, there is provided a method of treating HIV infections in a subject in need of such treatment comprising administering to the subject a therapeutically effective amount of a compound or composition of the invention, either alone or as an adjuvant, or complementary treatment to an existing anti-viral therapy.

In another aspect, there is provided formulations comprising the compound of the invention in combination with a pharmaceutically or veterinary or nutritionally acceptable carrier(s) or excipient(s).

In another aspect, the cost effective anti-viral or immune-supporting agent of the present invention is used during the maintenance phase of the treatment, following an initial viral load reduction phase in which it is used as an adjuvant to conventional anti-viral drug therapy.

In another aspect, this cost effective anti-viral or immune-supporting agent is used during the maintenance phase of the treatment, following an initial HIV load reduction phase in which it is used as an adjuvant to conventional anti-viral drug therapy.

In another aspect, the present composition is used for the treatment, prevention or management of immune-supporting system in primates, especially humans comprising administering an effective amount of plant extracts of *Withania somnifera* and *Mangifera indica* and an extract of purified Shilajit obtained from rock exudates.

DETAILED DESCRIPTION OF THE INVENTION

1. Description of the Poly-Herbal Composition

The polyherbal composition of the present invention contains the extracts of two plants *Withania somnifera* and *Mangifera indica* and an extract of rock exudates—purified Shilajit, A method for the treatment of viral infections is also disclosed. An effective amount of the polyherbal composition is administered one or more times a day either alone or as an adjuvant to an existing anti-viral therapy.

a. Extract of *Withania somnifera*

*Withania somnifera* Dunn., referred to as Ashwagandha in Ayurvedic medicine, is reputed for promoting health and longevity by increasing defense against disease, arresting the aging process, revitalizing the body in debilitating conditions. *W. somnifera* is also known to have positive effects on mental functions and memory, and can be classified in modem terminology as an adaptogen (Sharma, P. V. (1978). In *Dravyaguna Vijnan*, 4th edition, p. 763-765, Chaukhamba Sansthan, Varanasi, India; Ghosal, S. (1986). In pursuit of Standardization of Ayurvedic Drugs, *Ann. Natl. Acad. Ind. Med.*, 1, 1-14).

Typically, commercially available extracts of *Withania somnifera* lack the beneficial chemical constituents in appreciable quantities for which Aswhwagandha is reputed for, instead they contain:

Traces of glycowithanolide or completely devoid of glycowithanolides

Large amount of withanolide aglycones

High level of polysaccharides and low levels of oligosaccharides

Toxic tropane-type alkaloids, scopolamine

The quality of *W. somnifera* extract is improved by using the process reported in the U.S. Pat. Nos. 6,153,198 and 6,713,092 B1, which are herein incorporated by reference, and is a suitable process for obtaining the extract of *W. somnifera*. The extraction procedure provides a new and improved extract powder composition, which contains all the desired bioactive ingredients in optimized concentrations and ratios. The composition is stable, bio-available, and non-toxic.

Using this procedure, any parts of the plant of *W. somnifera* can be used in the present invention to obtain the extract provided it is devoid or have a trace amount of toxic tropane-type alkaloid, scopolamine. Preferred extract is the standardized extract containing glycowithanolides, withanolide agylcone and oligosaccharides and devoid or have a only a trace amount of toxic tropane-type alkaloid.

The extraction procedure of U.S. Pat. No. 6,153,198 provides: a high purity *Withania somnifera* plant extract composition with substantially low levels of cytotoxic withaferin A (aglycone), in the form of a stable, free-flowing light yellow-to-brown herbaceous powder composition, which provides enhanced cognition and augmented learning facility in the geriatric population when taken in a dosage of about 200-800 mg/day. The biologically-enhancing composition of the invention includes, by weight, (a) at least 3% of withanolide glycosides and sitoindosides, preferably 3-8%, (b) at least 3%, preferably 3-8%, of oligosaccharides, preferably a mol. wt. of <2000, and (c) less than 0.5% of free withaferin A (aglycone), wherein the ratio of (a):(c) is 75-95:25-5 and the ratio of (a):(b) is 40-60:60-40. Preferably, the composition is at least 90% soluble, the ash content of this composition is less than 8%, and its moisture content is less than 5% (w/w).

The standardized extract reported in U.S. Pat. No. 6,713,092 is contained in the following table:

TABLE 1

Standardized Withania Somnifera Extract Powder

| ANALYSIS | SPECIFICATION | RESULTS |
|---|---|---|
| Identity (HR) | HPLC - PDA spectrum | Confirms |
| i) Total withanolide glycoside conjugates (By HPLC) | ≧8% | 12.7% |

TABLE 1-continued

| | | |
|---|---|---|
| ii) Oligosaccharides (By HPTLC) | $\geq 25\%$ | 36.3% |
| iii) Free withaferin A and Equivalents - withanolide aglycones (By HPLC) | $\leq 2.0\%$ | 1.60% |
| Heavy Metals (as PB) | $\leq 0.002\%$ | Complies |
| Arsenic (As) | $\leq 0.0002\%$ | Complies |
| Sulfated Ash | $\leq 8\%$ | Complies |
| Moisture content | $\leq 5\%$ | 3.50% |
| Microbiological Test | | |
| Total Aerobic plate count | $<10^3/g$ | $2 \times 10^2$ CFU/gm |
| *Escherichia coli* | Absent in 1 g | Ni |
| *Salmonella* | Absent in 10 g | Nil |
| Ratio of withanolide glycoside conjugates and free withaferin A (aglycones) | 75-95 to 25-5 | 89:11 |
| Ratio of withanolide glycoside conjugates and oligosaccharides | 12-35 to 82-65 | 26:74 |

PRODUCT DESCRIPTION

| | |
|---|---|
| Appearance | Fine Powder |
| Color | Brown to brownish green |
| Odor | Characteristic |
| Taste | Mild bitter |
| Water-soluble extractive value | $\geq 80\%$ | b. Extract of *Mangifera indica*

*Mangifera indica* is widely found in many tropical and sub-tropical regions, and mango is one of the most popular edible fruits in the world. Aqueous decoction of mango stem bark has been traditionally used for the treatment of menorrhagia, scabies, diarrhea, syphilis, diabetes, cutaneous infection, and anemia. Chemical studies performed with this extract have enabled the isolation and identification of phenolic acids, phenolic esters, flavan-3-ols, mangiferin, which is the predominant component of this extract (A. Nunez-Selles, H. Velez-Castro, J. Aguero-Aguero, J. Gonzalez-Gonzalez, F. Naddeo, F. De Simone and L Rastrelli, J Agr Food Chem, 50:762-766, 2002).

Mangiferin (1,3,6,7-tetrahydroxyxanthone-C-2-β-D-glucoside) is a member of the C-glycosylxanthone family and is widely distributed in flowering plants. It has been isolated, in large amounts, from *Canscora decussata* Schult (family Gentianaceae) (Chaudhuri, R. K. and S. Ghosal, Chemical constituents of the Gentianaceae. I. Xanthones of *Canscora decussata* Schult. I., Phytochemistry, 10, 2425, 1971), *Swertia chirata* Buch.-Ham. (Gentianaceae) (Ghosal, S., P. V. Sharma and R. K. Chaudhuri, Chemical constituents of Gentianaceae. VII. Tetraoxygenated xanthones of *Swertia chirata*, S. J. Pharm. Sci., 62, 926-930, 1973), and *Mangifera indica* L. (Anacardiacea) (Ghosal, S., K. Biswas and B. K. Chattopadhyay, Toxic substances produced by *Fusarium*. VIII. Differences in the chemical constituents of *Mangifera indica* infected with *Asperigillus niger* and *Fusarium moniliforma*, Phytochemistry, 17, 689-694, 1978) (Ghosal, S., K. Biswas, and B. K. Chattopadhyay, Chemical constituents of *Mangifera indica*, Phytochemistry, 17, 689-694, 1978a), all of which are incorporated by reference.

Any parts of the plant of *M. indica* can be used in the present invention to obtain the extract. Preferably the extract contains at least 2% mangiferin and 2% mangiferin- and other xanthone glycosides along with other polyphenolics. Preferred standardized extract is obtained from *M. indica* bark. If needed, mangiferin from other plant sources can be blended with *M. indica* extract.

Preferred composition of the present invention includes an extract of *M. indica* bark comprising, by weight, (1) at least 2%, preferably to 5 to 10%, most preferably 11 to 25% of mangiferin, and (2) at least 1% mangiferin and other xanthone O-glycosides. Optionally, the *M. indica* extract of the present invention may contain other polyphenolics. The extract has about 70% water-soluble fraction.

c. Purified Shilajit

Shilajit is regarded as a panacea in many traditional systems of medicine, practiced worldwide. While many regard Shilajit as a potent immunomodulator and antioxidant, very few know what are the major bioactive constituents present in Shilajit. Purified Shilajit of the present invention composed of three distinct classes of bioactive compounds: (A) Low- and medium-Mw (mol. wt.) non-humic organic compounds, comprising free and conjugated (e.g., fattyacyl, aminoacyl, lipoidal) DBPs; (B) dibenzo-alpha-pyrones chromoproteins (DCPs) comprising: (i) dibenzo-alpha-pyrones or their derivatives, (ii) phosphocreatine, (iii) chromo-peptides of molecular weights of about $\leq 2$ KD and (iv) lipids having fatty acyl esters of glycerol; and (C) fulvic acids of low to medium molecular weight (Mn about 700 to 2,000). The fulvic acids are polymeric units of 3,8-oxygeneated dibenzo-alpha-pyrone (or derivatives) repeat units.

These three classes of compounds are essentially of marine animal origin,—fossil invertebrates, among which mollusks/Ammonites constitute the major contributors. Humification process and residence time on different rock surfaces would result in shilajit of different grades and composition of desirable and undesirable constituents. Hence, preferably the bioactive and supportive constituents of the shilajit are considered in the purification and standardization of shilajit.

Any process can be used to obtain purified Shilajit for the present inventive composition. Preferably the extract contains all three bioactive compounds (A, B and C) mentioned above and has substantially low levels of polymeric quinones and humus and humic acids.

2. Pharmaceutical or Veterinary or Nutritional Composition

While it is possible that, for use in therapy, poly-herbal blend of the invention may be administered as the raw chemical the preferred form for polyherbal composition is as active ingredients in a pharmaceutical formulation. Reference to active ingredients refers to the combined extracts of the two plants *Withania somnifera* and *Mangifera indica* and the extract of rock exudates—purified Shilajit The present invention further provides a pharmaceutical formulation comprising of the extracts of *Withania somnifera*, *Mangifera indica*, and Purified Shilajit and/or a pharmaceutically or veterinary or nutritionally acceptable excepient(s) and/or carrier(s), and optionally, other therapeutic and/or prophylactic ingredients are included. The excepient(s) and/or carrier(s) must be "acceptable" in the sense of being compatible with the other ingredients of the formulation and not deleterious to the recipient thereof.

Pharmaceutical or veterinary or nutritional formulations include those suitable for oral, nasal, topical (including buccal and sub-lingual), transdermal, or parenteral (including intramuscular, subcutaneous and intravenous) administration. The formulations may, where appropriate, be conveniently presented in discrete dosage units and may be prepared by any of the methods well known in the art of pharmaceutical or nutritional formulation. All methods preferably include the step of bringing into association the active compound with liquid carriers or finely divided solid carriers or both and then, if necessary, shaping the product into the desired formulation.

Alternatively pharmaceutical or veterinary or nutritional formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a powder or paste or suspension or solutions. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical or veterinary or nutritional polyherbal composition of the invention may also be formulated for parenteral administration (e.g., by injection, for example continuous infusion) and may be presented in unit dose form in ampoules, pre-filled syringes, small volume infusion or in multi-dose containers with an added preservative. The formulation may take such forms as suspensions, solutions, or emulsions in oily or aqueous vehicles, and may contain agents such as suspending, stabilizing an/or dispersing agents. Alternatively, the active ingredients may be in powder form, obtained by aseptic isolation of sterile solid or by lyophilisation from solution, for constitution with a suitable vehicle, e.g., sterile, pyrogen-free water, before use.

For topical administration to the epidermis, the pharmaceutical or veterinary or nutritional polyherbal composition the invention may be formulated as ointments, creams or lotions, or as a transdermal patch. Such transdermal patches may contain penetration enhancers such as linalool, carvacrol, thymol, citral, menthol, lecithin, diethylisosorbide, and alkylpyrrolidones. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active ingredients in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

When desired the above-described formulations adapted to give sustained release of the active ingredient may be employed.

The following examples are provided to illustrate various embodiments of the present invention and shall not be considered as limiting in scope.

EXAMPLES

A. Pharmaceutical/Nutritional Formulations

Example 1

Tablets and Capsules of the Inventive Polyherbal Composition

| | Ingredient | Quantity per Tablet/Capsule |
|---|---|---|
| 1. | Poly-Herbal Composition of the Invention | 0.05-100% by weight |
| 2. | Avicel pH 101 | 200.00 mg |
| 3. | Starch 1500 | 189.00 mg |
| 4. | Stearic acid, N.F. (powder) | 8.60 mg |
| 5. | Cab-O-Sil | 2.00 mg |

Note:
The target weight of tablet/capsule is 400 mg; Avicel pH 101 and Starch may be adjusted suitably to reach the target weight. The blended material can be filled into appropriate capsules.

Example 2

Tablets/Capsules with the Inventive Polyherbal Composition

| | Ingredient | Quantity per Tablet/Capsule |
|---|---|---|
| 1. | Poly-Herbal Composition of the Invention | 0.05-100% by weight |
| 2. | Cellulose | q.s. |
| 3. | Magnesium stearate | q.s. |
| 4. | Gelatin | q.s. |

Example 3

Tablets with the Inventive Polyherbal Composition

| | Ingredient | Quantity per Tablet/Capsule |
|---|---|---|
| 1. | Poly-Herbal Composition of the Invention | 0.5-30% by weight |
| 2. | Vitamin A (Beta Carotene) | 45,000 IU |
| 3. | Vitamin B-1 (Thiamin) | 25 mg |
| 4. | Inositol Hexanicotinate | 50 mg |
| 5. | Vitamin B-6 (Pyridoxine HCL) | 25 mg |
| 6. | Vitamin B-12 (Cyanocobalamin) | 500 mcg |
| 7. | Folic Acid | 800 mcg |
| 8. | Vitamin C (Magnesium Ascorbate) | 150 mg |
| 9. | Vitamin E D-alpha Tocophery (Natural) | 400 IU |
| 10. | Copper (Sebacate) | 750 mcg |
| 11. | Magnesium (Ascorbate, Taurinate, and Oxide) | 30 mg |
| 12. | Potassium (Citrate) | 10 mg |
| 13. | Selenium (L-Selenomethionine) | 200 mcg |
| 14. | Silica (from 400 mg of Horsetail Extract) | 10 mg |
| | Other Ingredients and Herbs: | |
| 15. | Coenzyme Q10 (Ubiquinone) | 10 mg |
| 16. | L-Carnitine L-Tartrate | 50 mg |

-continued

| | Ingredient | Quantity per Tablet/Capsule |
|---|---|---|
| 17. | Hawathorn Berry Extract | 40 mg |
| 18. | Grape Seed Extract | 10 mg |
| 19. | L-Proline | 50 mg |
| 20. | L-Lysine (HCL) | 50 mg |
| 21. | N-Acetyl Glucosamine | 50 mg |
| 22. | Bromelain (2,000 GDU per g) | 120 mg |
| 23. | Taurine (Magnesium Taurinate) | 50 mg |
| 24. | Inositol (Hexanicotinate) | 10 mg |

Example 4

Multi-Vitamin & Mineral Supplement Tablets with the Inventive Polyherbal Composition

| | Ingredient | Quantity per Tablet |
|---|---|---|
| 1. | Poly-Herbal Composition of the Invention | 0.5-30% by weight |
| 2. | Vitamin A (beta carotene) | 25,000 IU |
| 3. | Vitamin A (palmitate) | 10,000 IU |
| 4. | Vitamin B-1 (Thiamin Nitrate) | 10 mg |
| 5. | Vitamin B-2 (Riboflavin) | 10 mg |
| 6. | Inositol Hexanicotinate, Niacinamide & Niacin | 20 mg |
| 7. | Vitamin B-5 (Calcium D-Pantothenate) | 10 mg |
| 8. | Vitamin B-6 ((Phyridoxine HCL) | 10 mg |
| 9. | Vitamin B-12 (Cyanocobalamin) | 200 mcg |
| 10. | Biotin | 500 mcg |
| 11. | Folic Acid | 800 mcg |
| 12. | Vitamin C (Magnesium, Manganese & Zinc Ascorbates) | 180 mg |
| 13. | Fat-Soluble Vitamin C (from 476 mg of Ascorbyl Palmitate) | 20 mg |
| 14. | Vitamin D-3 (Cholecalciferol) | 400 IU |
| 15. | Vitamin E D-alpha Tocopheryl (Natural) | 600 IU |
| 16. | Boron (Amino Acid Chelate) | 2 mg |
| 17. | Calcium (Succinate, Carbonate, Malate) | 20 mg |
| 18. | Copper (Sebacate) | 1 mg |
| 19. | Iodine (from Kelp) 150 mcg, Magnesium (Ascorbate, Oxide, Succinate) | 150 mcg |
| 20. | Manganese (Ascorbate) | 30 mg |
| 21. | Molybdenum (Amino Acid Chelate) | 300 mcg |
| 22. | Potassium (Succinate, alpha-Ketoglutarate) | 10 mg |
| 23. | Selenium (L-Selenomethionine & Sodium Selenite) | 250 mcg |
| 24. | Zinc (Zinc Monomethionine & Ascorbate) | 10 mg |

Other Ingredients and Plant antioxidants: N-Acetyl Cysteine, Succinic Acid (Free Form), Choline (Bitartrate), Inositol (Hexanicotinate and Inositol), N-Acetyl Glucosamine, DMAE (Bitartrate), N-Acetyl L-Tyrosine, Coenzyme Q10, Alpha-Lipoic Acid, Quercetin, Milk Thisle Seed Extract, Grape Seed Extract, *Ginkgo Biloba*, Bilberry Extract.

Example 5

Anti-Diabetic Support Tablets/Capsules with the Inventive Polyherbal Composition

| | Ingredient | Quantity per Tablet/Capsule |
|---|---|---|
| 1. | Poly-Herbal Composition of the Invention | 0.5-30% by weight |
| 2. | Vitamin B-6 (as Pyridoxine HCl) | 10 mg |
| 3. | L-Arginine | 50 mg |
| 4. | L-Lysine Monohydrochloride | 50 mg |
| 5. | Cellulose | q.s. |
| 6. | Magnesium stearate | q.s. |
| 7. | Gelatin | q.s. |

Example 6

Weight Loss Support Tablets with the Inventive Polyherbal Composition

| | Ingredient | Quantity per Tablet/Capsule |
|---|---|---|
| 1. | Poly-Herbal Composition of the Invention | 0.5-30% by weight |
| 2. | *Garcinia Cambogia* Extract | 60 mg |
| 3. | Bitter Orange Peel Standardized Extract | 20 mg |
| 4. | Green Tea | 10 mg |
| 5. | Cayenne | 15 mg |
| 6. | Mustard Seed | 10 mg |
| 7. | Ginger Root | 10 mg |
| 8. | *Piper nigrum* | 10 mg |
| 9. | Acetyl L-Carnitine | 10 mg |
| 10. | Niacinamide | 10 mg |
| 11. | Vitamin B-6 (Pyridoxine HCl) | 10 mg |

Example 7

Chewable Tablets with the Inventive Polyherbal Composition

| Ingredient No. | Ingredient | Composition (% w/w) |
|---|---|---|
| 1. | Poly-Herbal Composition of the Invention | 0.5-30 |
| 2. | Sodium ascorbate, USP | 12-35 |
| 3. | Avicel pH 101 | 5-15 |
| 4. | Sodium saccharin, N.F. (powder) | 0.56 |
| 5. | DiPac | 10-30 |
| 6. | Stearic acid, N.F | 2.50 |
| 7. | Imitation orange flavor | 1.00 |
| 8. | FD&C Yellow#6 dye | 0.50 |
| 9. | Cab-O-Sil | 0.50 |

Procedure: Blend all the ingredients, except 6, for 20 min. in a blender. Screen in 6 and blend for an additional 5 min. Compress into tablets using 7/16-in standard concave tooling.

Example 8

Syrup with the Inventive Polyherbal Composition

| Ingredient No. | Ingredient | Quantity per 100 mL |
|---|---|---|
| 1. | Poly-Herbal Composition of the Invention | 0.5-30% by volume |
| 2. | Excipients | q.s |

Example 9

Oral Liquid with the Inventive Composition

| | Ingredient | Quantity per 100 ml |
|---|---|---|
| 1. | Poly-Herbal Composition of the Invention | 0.5-30% by volume |
| 2. | Purified Water | q.s. |
| 3. | Excipients: Preservatives, stabilizers, sweeteners, flavors, colors, etc. | q.s. |

Example 10

Snack Bar with the Inventive Polyherbal Composition

| Ingredient No. | Ingredient | Quantity per 1 Kg |
|---|---|---|
| 1. | Poly-Herbal Composition of the Invention | 0.5-30% by weight |
| 2. | Nutrition Blend: Calcium (Tricalcium Phosphate and Calcium Carbonate), Magnesium (Magnesium Oxide), Vitamin A, Vitamin C, Vitamin D-3, Vitamin B-1 (Thiamin), Vitamin B-2 (Riboflavin), Vitamin B-6 (Pyridoxine), Vitamin B-12 (Cyanocobalamin), Natural Vitamin (Acetate), Niacin, Biotin, Pantothenic Acid, Zinc, Folic Acid, Vitamin K, Selenium. Other Ingredients: Protein Blend (Soy protein isolate, Hydrolyzed collagen, Whey protein isolate, Calcium/Sodium Caseinate), Glycerine, Polydextrose (fiber), Water, Cocoa Butter, Natural Coconut Oil (non-hydronated), Coconut, Cellulose, Cocoa Powder, Olive Oil, Lecithin, Natural and Artificial Flavor, Maltodextrin, Guar Gum, Citric Acid (Flavor Enhancer), Sucralose | q.s |

Example 11

Cereal with the Inventive Polyherbal Composition

| Ingredient No. | Ingredient | Quantity per 1 Kg |
|---|---|---|
| 1. | Poly-Herbal Composition of the Invention | 0.5-30% by weight |
| 2. | Excipients: Whole Grain Oats, Oat Bran, Sugar, Modified Corn Starch, Brown Sugar Syrup, Salt, Calcium Carbonate, Trisodium Phosphate, Wheat Flour, Vitamin E (Mixed tocopherols), Zinc & Iron (Mineral nutrients), Niacinamide (A B Vitamins), Vitamin B6 (Pyridoxine Hcl), Vitamin B2 (Riboflavin), Vitamin B1 (Thiamin Mononitrate), Vitamin A (Palmitate), Vitamin A B (Folic acid), Vitamin B12, Vitamin D | q.s |

Example 12

Beverage with the Inventive Polyherbal Composition

| Ingredient No. | Ingredient | Quantity per 500 mL |
|---|---|---|
| 1. | Poly-Herbal Composition of the Invention | 0.5-30% by volume |
| 2. | Excipients: Filtered Water, Food Starch-Modified, Citric Acid, Bitter Orange, Green Tea Extract, Maltodextrin, Whey Protein Isolate, High Fructose Corn Syrup and/or Sucrose and/or Sugar, Sodium Benzoate, Caffeine, Niacin, Glycerol Ester of Wood resin, Flavors, Colors | q.s |

B. Veterinary Formulations

Example 13

Chewable Tablets with the Inventive Polyherbal Composition

| Ingredient No. | Ingredient | Composition |
|---|---|---|
| 1. | Poly-Herbal Composition of the Invention | 0.5-30% w/w |
| 2. | Calcium (from calcium phosphate) | 600 mg |
| 3. | Phosphorus (from calcium phosphate) | 470 mg |
| 4. | Vitamin C | 10 mg |
| 5. | Vitamin A | 750 I.U. |
| 6. | Vitamin D3 | 400 I.U. |
| 7. | Excipients | q.s. |

Note:
Administer free choice just prior to feeding, or crumble and mix with food

Example 14

Vitamin Tablets with the Inventive Polyherbal Composition (Peanut Butter Flavor)

| | Ingredient | Quantity per Tablet |
|---|---|---|
| 1. | Poly-Herbal Composition of the Invention | 0.05-50% by weight |
| 2. | Other Ingredients: Brewer's Yeast Powder, Garlic, Whey, Beef Liver, Peanut Butter, Silica Gel, Niacin, Riboflavin, Thiamine Mononitrate, Ascorbic acid | q.s. |

Example 15

Granules with the Inventive Polyherbal Composition

| | Ingredient | Quantity per 4 oz. |
|---|---|---|
| 1. | Poly-Herbal Composition of the Invention | 0.05-100% by weight |
| 2. | Other Ingredients: Potassium Gluconate, Wheat, Sucrose, Hydrolyzed Vegetable Protein, Silicone Dioxide, TBHQ (preservative) | q.s. |

Example 16

Blood-Building Powder with the Inventive Polyherbal Composition

| | Ingredient | Quantity per lb. |
|---|---|---|
| 1. | Poly-Herbal Composition of the Invention | 0.05-50% by weight |
| 2. | Other Ingredients: Heme iron polypeptide, Niacin (Vitamin B3), Vitamin E acetate, Riboflavin (Vitamin B2), Thiamine (Vitamin B1), Pyridoxine (Vitamin B6), Vitamin B12, Copper Sulfate, Cobalt sulfate, Soybean oil, Whey, Natural sweet apple and molasses flavors | q.s. |

Example 17

Liquid Capsules with the Inventive Polyherbal Composition

| | Ingredient | Quantity per Capsule |
|---|---|---|
| 1. | Poly-Herbal Composition of the Invention | 0.05-50% by weight |
| 2. | Other Ingredients: Safflower Oil, Gelatin, Fish Oil, Glycerin, Borage Seed Oil, Vitamin E, Water | q.s. |

Note:
The capsules may be punctured and the liquid contents squeezed onto food, if desired.

Example 18

Oral Liquid with the Inventive Polyherbal Composition

| | Ingredient | Quantity per 100 ml |
|---|---|---|
| 1. | Poly-Herbal Composition of the Invention | 0.05-50% by volume |
| 2. | Purified Water, Sugar, Sorbitol, Polysorbate 80, Propylene glycol, Peptones, Ferric ammonium citrate, nicotinamide, Vitamin A and D3 concentrate, d-panthenol, Thiamine Hcl (Vitamin B1), alpha tocopheryl acetate (Vitamin E), saccharine sodium, Vitamin A palmitate, Pyridoxine Hcl (Vitamin B6), Riboflavin 5'-Phosphate sodium (source of Vitamin B2) | q.s. |

Example 19

Suspension with the Inventive Polyherbal Composition

| Ingredient No. | Ingredient | Quantity per each oz. |
|---|---|---|
| 1. | Poly-Herbal Composition of the Invention | 0.10-50.00% |
| 2. | Fat (Polyunsaturated) | 45% |
| 3. | Carbohydrate | 33% |
| 4. | Vitamin A | 500 I.U. |
| 5. | Vitamin D3 | 40 I.U. |
| 6. | Vitamin E | 3 I.U. |
| 7. | Thiamine Hcl (Vitamin B1) | 0.15 mg |
| 8. | Riboflavin 5'Phos Na (Vitamin B2) | 0.17 mg |
| 9. | Pyridoxine Hcl (Vitamin B6) | 0.2 mg |
| 10. | Ascorbic acid (Vitamin C) | 6.0 mg |
| 11. | Nicotinamide | 2.0 mg |
| 12. | Pantothenic acid | 1.0 mg |
| 13. | Folic acid | 0.04 mg |
| 14. | Sodium Benzoate | 0.1% |

Example 20

Injectable with the Inventive Composition

| | Ingredient | Quantity per ml |
|---|---|---|
| 1. | Poly-Herbal Composition of the Invention | 0.1-10% by volume |
| 2. | Water for Injection, USP | q.s. |
| 3. | Ingredients to maintain proper pH | q.s. |

A. Efficacy Studies: Reduction of Viral Loads and Boosting of Immune-System

Efficacy studies were conducted which illustrated the favorable effect that the administration of the polyherbal composition has in patients with HIV infection. The composition resulted in a decreased mean viral load, which was associated with good symptomatic improvement.

Example 21

Material and Methods

Patients and Methods: In the present open label, pilot study, patients who were diagnosed clinically and confirmed HIV status by positive ELISA and Westernblot test were enrolled. The study protocol was approved by an Ethical Committee. Each patient was explained about the available treatment options and was asked to give written informed consent for the present study. The identity and all information pertaining to the patients were kept confidential. Patients of either gender between the age groups of 20-60 years who are positive for HIV infection confirmed by ELISA and Westernblot were enrolled to receive the treatment. Asymptomatic patients or patients with mild to moderate symptoms and signs of HIV infection, and CD4 count of less than 500 cells were enrolled. Patients who gave informed consent and also assurance for attending regular follow-up only were included. Patients with severe and progressive AIDS, patients on other antiretroviral therapy, those on other herbal preparations, patients with abnormal renal, hepatic biochemical parameters or total WBC count less than 2000 cells/cu mm were excluded from the study. Patients with severe active infection requiring hospitalization within the previous two weeks and patients on other immunomodulators were also excluded. Patients received treatment if they had any opportunistic infection like Tuberculosis, Candidiasis etc. No antiretroviral drug from allopathic or alternative system of medicine was permitted.

Drug treatment and follow-up: The polyherbal capsule administered in the study contained extracts of each of the following—*Withania somnifera* (100 mg), *Mangifera indica* (100 mg) and purified Shilajit (100 mg). Patients took two capsules of the test drug twice daily with 200 ml of water. Each patient was evaluated by he same investigator at 0,1,3,6,9,12,16,20, and 24 months throughout the study.

Patient Evaluation: All patients were thoroughly evaluated clinically to satisfy inclusion/exclusion criteria before the enrolment. Complete demographic data including source of possible infection, mode of infection, duration and main complaints were recorded on case record form (CRF). Vital signs and frequency and severity of various symptoms indicating HIV infection like loss in body weight, fever, diarrhea, anorexia, fatigue, weakness, nausea, vomiting, herpes, oral thrush, bleeding diathesis, cough, genital ulceration and any other symptom complained by the patient were recorded and evaluated by using a 4-point scale, where 0=none, 1=mild, 2=moderate and 3=severe. The frequency and severity of all the symptoms were also assessed. Presence of opportunistic infections like tuberculosis, candidiasis, herpes, CMV, toxoplasmosis, lymphomas and Pneumocystis caranii were evaluated by performing suitable radiological and serological investigations. In each patient, performance index was assessed by Karnofsky score ranging from 0-100, where 0—represented a moribund patient and 100—a normal patient (Karnofsky D and Burchenal J H. Clinical evaluation of chemotherapeutic agents in cancer. In Macleod C M. (ed) Evaluation of chemotherapeutic agents. Columbia University Press, New York 1949; 199-205).

Objective parameters for evaluation: Lymphocyte phenotyping was carried out using the flow cytometry technique before and every 6 months during drug treatment to evaluate the immunological status of the patient. Quantitative estimation of HIV viral load employing RNA PCR technique was carried out before and at 6 and 12 months treatment with the test polyherbal composition in some patients chosen at random (using random tables).

Safety and tolerability evaluation: Routine hematological, biochemical, hepatic and renal laboratory parameters were estimated before and after every 6 months of therapy. Incidence of any adverse reaction reported by patient or on direct questioning by the investigator were recorded in the CRF at every visit.

Patient compliance: Patients were enquired at each visit about all medications taken. Pill count method was used to monitor patient compliance and was measured using 4 point scale where 3=Excellent (drug consumption more than 90%), 2=Good (drug consumption between 81-90%), 1=Fair (drug consumption between 65-80% and 0=poor (drug consumption less than 65%).

Global evaluation: Physician's and patient's global evaluation of the treatment was assessed using 4 point scale where 0=Poor, 1=Fair, 2=Good and 3=Very good at the end of every 6 months treatment period.

Statistical analysis: All values are presented as Mean with 95% CI. ANOVA and paired "t" test were used to analyse the difference with treatment in change of body weight, viral load content, CD4 and CD8 cell counts. All statistical tests were two-sided and significance was defined as $p<0.05$ at 95% CI.

Results of the Study

In the present open study, total 19 patients (3F; 16 M), mean age 29.7±5.6 years (range: 42.0-22.0), mean weight 61.7±10.3 Kg (range: 37.0-78.0) and with mean duration of AIDS defining illness 126.8 days were enrolled to evaluate the efficacy and safety of new polyherbal composition. None of the patients received any anti-retroviral drugs. One patient died, and one was lost for follow up at the end of 6 months therapy. Seventeen and twelve patients completed 6 and 12 months therapy respectively.

Mean body weight increased from 61.7±10.3 Kg (basal) to 63.88±10.6 Kg, and 64.1±11.47 Kg respectively after 6 and 12 months treatment. Fatigue, anorexia, fever, cough, and skin rash were the most common presenting symptoms. Treatment with the herbal drug reduced incidence and severity of symptoms. There was marked improvement in symptoms like myalgia, fever, cough, and anorexia with treatment. Highly significant improvement was noticed in the Karnofsky score from baseline value of 80 (60-100) to 85 (70-100), and 90 (80-100) at the end of 6, and 12 months respectively.

Treatment with the test polyherbal composition produced a decrease in the mean viral load from 61,293±32,639 copies/ml (range: 10,517-135,353) (n=19) to 49,533±30,777 copies/ml (range: 20-99,050) (n=16) and 19,440±22,146 copies/ml (range: 823-65,983) (n=7) after 6 and 12 months treatment respectively. The mean % decrease in viral load was 19 & 68% after 6 & 12 months treatment.

There was no significant alteration in other hematological, hepatic or renal functions. Compliance was excellent or good in 95% patients to the test medication. Except mild gastrointestinal symptoms, all patients tolerated the drug well and no subject discontinued therapy due to side effects. In global evaluation of treatment, every patient and physician rated the effects of the drug in the categories. The overall effect of herbal drug was rated very effective or effective in more than 80% patients by physician, while patients rated treatment as excellent or good by 76% and 100% respectively after 6 and 12 months.

This example illustrates the effectiveness of the polyherbal composition of the present invention as an anti-viral agent. It is to be understood that the above-described embodiments and example are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A polyherbal composition for the treatment of viral infections caused by human immunodeficiency virus (HIV) comprising:
   i. an effective amount of plant extracts of *Withania somnifera* and *Mangifera indica*; and,
   ii. an extract of purified Shilajit obtained from rock exudates
   wherein said plant extract of *Mangifera indica* comprises mangiferin and glycosides of mangiferin and of other xanthones and, optionally, polyphenolics.

2. An anti-viral formulation comprising:
   i. the composition of claim 1; and
   ii. one or more pharmaceutically or veterinary or nutritionally acceptable excipients.

3. The formulation of claim 2 wherein the formulation is in the form of one of liquids, powders, pills, tablets, capsules and confectionery bars.

4. The composition of claim 1 wherein the extracts of *Withania somnifera* and *Mangifera indica* and an extract of purified Shilajit are standardized.

5. The composition of claim 1 wherein the composition is in a dosage form suitable for oral administration further comprising excipients suitable for such oral administration.

6. The composition of claim 5 wherein the composition is in one of the form of liquids, powders, pills, tablets, capsules or confectionery bars.

7. The composition of claim 1 further comprising a pharmaceutically or veterinary or nutritionally acceptable excipient thereby to form a formulation.

8. The formulation of claim 7 wherein the excipient is pharmaceutically or nutritionally acceptable and the composition is in a dosage of about 50 mg to about 5,000 mg once or twice a day for a human.

9. A polyherbal composition for adjuvant therapy to an existing human immunodeficiency virus (HIV) therapy comprising:
   i. an effective amount of plant extracts of *Withania somnifera* and *Mangifera indica*; and
   ii. an extract of purified Shilajit obtained from rock exudates,
   wherein said plant extract of *Mangifera indica* comprises mangiferin and glycosides of mangiferin and of other xanthones and, optionally, polyphenolics.

10. An anti-viral formulation for adjuvant therapy to an existing anti-viral therapy comprising:
    i. the composition of claim 9; and
    ii. one or more pharmaceutically or veterinary or nutritionally acceptable excipients.

11. The formulation of claim 10 wherein the formulation is in the form of one of liquids, powders, pills, tablets, capsules and confectionery bars.

12. The composition of claim 9 wherein the extracts of *Withania somnifera* and *Mangifera indica* and an extract of purified Shilajit are standardized.

13. The composition of claim 12 wherein the standardized extract of *Withania somnifera* comprises withanolide glycoside conjugates at $\geq 8\%$, free Withaferin A (aglycone) at $\leq 2.0\%$ and oligosaccharides at $\geq 25\%$.

14. The composition of claim 13 wherein the standardized extract of shilajit comprises oxygenated dibenzo-α-pyrones, dibenzo-α-pyrone chromoproteins and fulvic acid.

15. The composition of claim 12 wherein the standardized extract of shilajit comprises oxygenated dibenzo-α-pyrones, dibenzo-α-pyrone chromoproteins and fulvic acid.

16. The composition of claim 9 wherein the composition is in a dosage form suitable for oral administration further comprising excipients suitable for such oral administration.

17. The composition of claim 16 wherein the composition is in one of the form of liquids, powders, pills, tablets, capsules or confectionery bars.

18. The composition of claim 9 further comprising a pharmaceutically or veterinary or nutritionally acceptable excipient to form a formulation.

19. The formulation of claim 18 wherein the excipient is pharmaceutically or nutritionally acceptable and the composition is in a dosage of about 50 mg to about 5,000 mg once or twice a day for a human.

20. A polyherbal composition for adjuvant therapy to an existing human immunodeficiency virus (HIV) therapy comprising:
    i. an effective amount of plant extracts of *Withania somnifera* and *Mangifera indica*: and
    ii. an extract of purified Shilajit obtained from rock exudates, wherein the extracts of *Withania somnifera* and *Mangifera indica* and an extract of purified Shilajit are standardized and wherein the standardized extract of *Mangifera indica* comprises mangiferin and glycosides of mangiferin and of other xanthones and polyphenolics.

21. A polyherbal composition for adjuvant therapy to an existing human immunodeficiency virus (HIV) therapy comprising:
    i. an effective amount of plant extracts of *Withania somnifera* and *Mangifera indica*; and
    ii. an extract of purified Shilajit obtained from rock exudates,
    wherein the extracts of *Withania somnifera* and *Mangifera indica* and an extract of purified Shilajit are standardized, wherein the standardized extract of *Mangifera indica* comprises mangiferin and glycosides of mangiferin and of other xanthones and polyphenolics.

* * * * *